US009551713B2

(12) United States Patent
Kamat et al.

(10) Patent No.: US 9,551,713 B2
(45) Date of Patent: Jan. 24, 2017

(54) USE OF A PANEL OF URINARY CYTOKINES TO PREDICT RESPONSE TO BCG THERAPY FOR BLADDER CANCER

(71) Applicant: Board of Regents, The University of Texas System, Austin, TX (US)

(72) Inventors: Ashish M. Kamat, Houston, TX (US); Joseph Briggman, Westford, MA (US); Colin P. Dinney, Houston, TX (US); Diana Urbauer, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 14/382,374

(22) PCT Filed: Mar. 4, 2013

(86) PCT No.: PCT/US2013/028891
§ 371 (c)(1),
(2) Date: Sep. 2, 2014

(87) PCT Pub. No.: WO2013/131093
PCT Pub. Date: Sep. 6, 2013

(65) Prior Publication Data
US 2015/0212090 A1 Jul. 30, 2015

Related U.S. Application Data

(60) Provisional application No. 61/605,947, filed on Mar. 2, 2012.

(51) Int. Cl.
*G01N 33/574* (2006.01)
*A61K 35/74* (2015.01)
*A61N 5/10* (2006.01)
*G06F 19/00* (2011.01)

(52) U.S. Cl.
CPC ......... *G01N 33/57488* (2013.01); *A61K 35/74* (2013.01); *A61N 5/10* (2013.01); *G01N 33/57407* (2013.01); *G06F 19/3487* (2013.01); *G01N 2333/52* (2013.01); *G01N 2333/54* (2013.01); *G01N 2333/545* (2013.01); *G01N 2333/5412* (2013.01); *G01N 2333/5434* (2013.01); *G01N 2333/57* (2013.01); *G01N 2333/70575* (2013.01); *G01N 2800/52* (2013.01)

(58) Field of Classification Search
CPC .................................................... A61K 35/74
See application file for complete search history.

(56) References Cited

U.S. PATENT DOCUMENTS

2003/0032074 A1   2/2003   Slawin et al.

OTHER PUBLICATIONS

Han et al. Korean J Urol., 2009, 50:1037-1047.*

Jackson et al., "Changes in urinary cytokines and soluble intercellular adhesion molecule-1 (ICAM-1) in bladder cancer patients after Bacillus Calmette-Guérin (BCG)," *Clin Exp Immunol.*, 99:369-375, 1995.
Jackson et al., "Prognosis of intravesical bacillus calmette-guerin therapy for superficial bladder cancer by immunological urinary measurements: statistically weighted syndromes analysis," *The Journal of Urology*, 159:1054-1063, 1998.
Partial Supplementary European Search Report issued in European Application No. 13755291.5, mailed Sep. 24, 2015.
Watanabe et al., "Urinary interleukin-2 may predict clinical outcome of intravesical bacillus Calmette-Guérin immunotherapy for carcinoma in situ of the bladder," *Cancer Immunol. Immunother.*, 52:481-486, 2003.
De Reijke et al., "Urinary cytokines during intravesical bacillus calmette-guerin therapy for superficial bladder cancer: processing, stability and prognostic value," *The Journal of Urology*, 155(2):477-482, 1996.
Esuvaranathan et al., "Interleukin-6 production by bladder tumors is upregulated by BCG immunotherapy," *J. Urol.*, 154(2 Pt 1):572-575, 1995.
Galea et al., "The Nottingham Prognostic Index in primary breast cancer," *Breast Cancer Res Treat.*, 22(3):207-219, 1992.
Johnson, "Pharmacogenetics: potential for individualized drug therapy through genetics," *Trends in Genetics*, 19(11):660-666, 2003.
Kamat et al., "Cytokine panel for response to intravesical therapy (CyPRIT): nomogram of changes in urinary cytokine levels predicts patient response to bacillus Calmette-Guérin," *Eur Urol.*, In Press, 2015.
Kamat et al., "Use of fluorescence in situ hybridization to predict response to Bacillus Calmette-Guérin therapy for bladder cancer: results of a prospective trial," *Journal of Urology*, 187(3):862-867, 2012.
Kattan et al., "Postoperative nomogram for disease recurrence after radical prostatectomy for prostate cancer," *J. Clin Oncol.*, 17(5):1499-1507, 1999.
Lamm et al., "Maintenance bacillus Calmette-Guerin immunotherapy for recurrent TA, T1 and carcinoma in situ transitional cell carcinoma of the bladder: a randomized Southwest Oncology Group Study," *J. Urol.*, 163(4):1124-1129, 2000.
Ludwig et al., "Tumor necrosis factor-related apoptosis-inducing ligand: a novel mechanism for Bacillus Calmette-Guérin-induced antitumor activity," *Cancer Research*, 64(10):3386-3390, 2004.
PCT International Preliminary Report on Patentability issued in International Application No. PCT/US2013/028891, mailed Sep. 12, 2014.
PCT International Search Report and Written Opinion issued in International Application No. PCT/US2013/028891, mailed Jun. 12, 2013.
Rabinowitz et al., "Urinary interleukin-8/creatinine level as a predictor of response to intravesical bacillus Calmette-Guerin therapy in bladder tumor patients," *J. Urol.*, 158(5):1728-1731, 1997.

(Continued)

*Primary Examiner* — Bin Shen
(74) *Attorney, Agent, or Firm* — Parker Highlander PLLC

(57) ABSTRACT

Methods for predicting cancer recurrence following a BCG immunotherapy are provided. In some aspects, cytokine levels from a patient are measured before and after a BCG therapy and the changes in cytokine levels are used to determine the risk of cancer lapse. Methods for selecting a patient for a further anti-cancer therapy are also provided.

11 Claims, 6 Drawing Sheets

(56) References Cited

OTHER PUBLICATIONS

Rouzier et al., "Nomograms to predict pathologic complete response and metastasis-free survival after preoperative chemotherapy for breast cancer," *Journal of Clinical Oncology*, 23(33):8331-8339, 2005.

Saint et al., "Do prognostic parameters of remission versus relapse after Bacillus Calmette-Guérin (BCG) immunotherapy exist? Analysis of a quarter century of literature," *Eur Urol.*, 43(4):351-360, 2003.

Saint et al., "Prognostic value of a T helper 1 urinary cytokine response after intravesical bacillus calmette-guerin treatment for superficial bladder cancer," *The Journal of Urology*, 167(1):364-367, 2002.

Savic et al., "The prognostic value of cytology and fluorescence in situ hybridization in the follow-up of nonmuscle-invasive bladder cancer after intravesical Bacillus Calmette-Guérin therapy," *Int. J. Cancer*, 124(12):2899-2904, 2009.

Shariat et al., "Critical review of prostate cancer predictive tools," *Future Oncol.*, 5(10):1555-1584, 2009.

Stephenson et al., "Postoperative nomogram predicting the 10-year probability of prostate cancer recurrence after radical prostatectomy," *J Clin Oncol.*, 23(28):7005-7012, 2005.

Sylvester et al., "Predicting recurrence and progression in individual patients with stage Ta T1 bladder cancer using EORTC risk tables: a combined analysis of 2596 patients from seven EORTC trials," *European Urology*, 49(3):466-475; discussion 475-477, 2006.

Thalmann et al., "Interleukin-8 expression in the urine after bacillus Calmette-Guerin therapy: a potential prognostic factor of tumor recurrence and progression," *J. Urol.*, 158:1340-1344, 1997.

Thalmann et al., "Urinary interleukin-8 and 18 predict the response of superficial bladder cancer to intravesical therapy with bacillus calmette-guerin," *The Journal of Urology*, 164(6):2129-2133, 2000.

\* cited by examiner

USE OF A PANEL OF URINARY CYTOKINES TO PREDICT RESPONSE TO BCG THERAPY FOR BLADDER CANCER

The present application is a national phase application under 35 U.S.C. §371 of International Application No. PCT/US2013/028891, filed Mar. 4, 2013, which claims the priority benefit of U. S. provisional application No. 61/605,947, filed Mar. 2, 2012, the entire contents of each of which are incorporated herein by reference.

BACKGROUND OF THE INVENTION

1. Field of the Invention

The present invention relates generally to the field of molecular biology, immunology and oncology. More particularly, it concerns diagnostic methods for predicting a response to an immunotherapy.

2. Description of Related Art

More than 70,000 new cases of bladder cancer are diagnosed yearly, with the majority presenting as superficial, i.e. non-muscle-invasive bladder cancer (NMIBC) (Jemal et al., 2010). Non-muscle invasive bladder cancer (NMIBC) accounts for about 75% of newly diagnosed cases, and comprise a heterogeneous group whose individual prognoses are difficult to predict. Sixty percent to 70% of non-muscle invasive tumors recur and 10% to 40% progress to muscle-invasive disease (Heney et al., 1983). The standard treatment for NMIBC is transurethral resection followed by adjuvant intravesical therapy with BCG (*Bacillus* Calmette Guerin), the most effective intravesical treatment, for high-risk patients (Kamat and Lamm, 2001); however, a significant number of patients fail treatment (70% tumor recurrence) and require more aggressive intervention, such as radical cystectomy and/or chemotherapy. Currently, post-transurethral resection (TUR) surveillance is performed by cystoscopy and urine cytology at regular intervals. As such, clinicopathological variables remain the only prognostic predictors and these include tumor grade, tumor stage, tumor size, number of tumors, and location of the tumors. These variables rely on detection of actual tumor recurrence and are poor predictors of therapy failure making it hard to predict the effectiveness of therapy prior to recurrence of the tumor (Dalbagni et al., 1999; Highshaw et al., 2003). If patients do not respond to intravesical BCG, performing radical cystectomy within the first 24 months after diagnosis is believed to improve survival by at least 20% (Herr and Sogani, 2001). The ability to preemptively identify patients who are destined to recur will have tremendous impact since it would allow clinicians to provide patients with a tailored approach to their disease and provide individualized knowledge of whether their treatment is efficacious. Thus, early identification of patients in whom BCG will fail would allow those patients to receive earlier curative radical cystectomy and improve their chances of survival. New minimally invasive tests are clearly needed to increase the accuracy of prediction of recurrence, especially in patients treated with BCG.

SUMMARY OF THE INVENTION

In a first embodiment there is provided a method for predicting a response to a Mycobacterial-based immunotherapy, such as a *Bacillus* Calmette-Guerin (BCG)-based anticancer therapy in a cancer patient. For example, in some aspects, a method is provided for predicting a response in a patient suffering from bladder carcinoma to treatment with BCG by using a panel of cytokines. These methods and associated devices may be used for personalized risk prediction to the individual patient.

In one embodiment, the present invention provides a method to predict a prognosis in a cancer patient following a BCG therapy, comprising obtaining at least two samples from the patient, at least one before and one after BCG therapy; measuring changes in the levels of at least 3 cytokines in the samples, said at least 3 cytokines selected from the group consisting of IL-2, IL-6, IL-8, IL-18, IL-1ra, IL-1B, TRAIL, IL-10, IFN-γ, IL-12(p70), IL-12(p40) and TNF-α; and identifying whether the patient is at risk for relapse based on the measured changes in cytokine levels. In one aspect, the method comprises measuring changes in the levels of 4, 5, 6, 7, 8, 9, 10, 11 or 12 cytokines selected from the group consisting of IL-2, IL-6, IL-8, IL-18, IL-1ra, IL-1B, TRAIL, IL-10, IFN-γ, IL-12(p70), IL-12(p40) and TNF-α in the samples and identifying whether the patient is at risk for relapse based on the measured changes in cytokine levels. In another aspect, the method comprises measuring changes in the levels of IL-2, IL-6, IL-8, IL-18, IL-1ra, IL-1B, TRAIL, IL-10, IFN-γ, IL-12 (p70), IL-12 (p40), and TNF-α in the samples and identifying whether the patient is at risk for relapse based on the measured changes in cytokine levels. In yet another aspect, the method comprises measuring changes in the levels of IL-2, IL-6, IL-8, IL-18, IL-1ra, TRAIL, INF-γ, IL-12 (p70), and TNF-α in the samples and identifying whether the patient is at risk for relapse based on the measured changes in cytokine levels.

In certain aspects, samples for use according to the embodiments are urine samples. In other aspects, the samples may be blood or tissue samples. In certain aspects, the cancer patient has an epithelial cancer, such as a melanoma or a bladder cancer. For example, in some aspects, the patient has a bladder cancer such as a non-muscle-invasive bladder cancer.

As used herein the term Mycobacterial-based immunotherapeutic refer to administration of a strain of *Mycobacterium* that is not typically pathogenic in a human with an intact immune system. For some applications, attenuated Mycobacteria comprise live bacteria that are capable of active proliferation. Thus, the dosage of such Mycobacteria may be quantified by the number live bacteria colonies that can be formed when the bacteria are allowed to proliferate. A variety of species and strains of attenuated Mycobacteria may be used according to the embodiments. For example, in certain aspects, the Mycobacteria is attenuated is *Mycobacterium bovis*. In certain particular cases the attenuated *Mycobacterium bovis* is the Bacille Calmette-Guerin (BCG) *Mycobacterium bovis*. In some other aspects, the attenuated Mycobacteria may be the TICE™ BCG, Pasteur or Rijksinstituut voor Volksgezondheid en Milieuhygiene (RIVM) strain of bacteria.

In methods of the instant embodiments, attenuated Mycobacterial compositions can be administered in a variety of ways. For example in some cases the attenuated Mycobacteria are administered intratumorally, subcutaneously, cutaneously or intradermally. In some aspects, a Mycobacteria (e.g., BCG) therapy is an intravesical BCG therapy (e.g., as bladder cancer therapy).

Certain aspects of the embodiments concern measuring the level cytokines in a sample. Cytokine levels can, for example, be measured directly by assessing cytokine protein levels in a sample. For instance, cytokine levels can be measure, by Western blot or ELISA. In other aspects, the mRNA expression levels of various cytokines can be measured. For example, mRNA expression levels can be measured by RT-PCR, Northern blot or array hybridization.

In some aspects, identifying whether the patient is at risk for relapse comprises determining a point value for each of the changes in cytokine levels and correlating the total points value with a value on the predictor scale. In certain aspects, the determining and/or correlating is performed by a computer.

In some aspects, a method of the embodiments further comprises reporting whether the patient is at risk for relapse or reporting the cytokine levels (or change in cytokine levels of the patient). Reporting may comprise preparing a written, oral or electronic report. The report may be provided, for example, to the patient, a doctor, a hospital or an insurance company.

Another embodiment of the present invention provides a method of treating a patient comprising selecting a patient at risk for cancer relapse following a BCG by measuring changes in cytokine levels as described above, and administering an anti-cancer therapy the patient. In certain aspects, the anti-cancer therapy is a further BCG therapy. The anti-cancer therapy may also be a chemotherapy, a radiation therapy or a surgical therapy.

A further embodiment of the present invention provides a nomogram useful to predict the likelihood of developing bladder carcinoma in a patient. The nomogram is constructed using a panel of urinary cytokines. In certain aspects, the nomogram is predictive of the patient's response to intravesical immunotherapy with *Bacillus* Calmette Guerin (BCG). In certain aspects, the nomogram is generating using a panel of urinary cytokines comprising the levels of at least 3 cytokines selected from the group consisting of IL-2, IL-6, IL-8, IL-18, IL-1ra, IL-1B, TRAIL, IL-10, IFN-γ, IL-12(p70), IL-12(p40) and TNF-α. In other aspects, the panel of urinary cytokines may comprise the levels of at least 4, 5, 6, 7, 8, 9, 10 or 11 of said cytokines. In certain aspects, the nomogram is a nomogram provided as FIG. 3 or FIG. 6.

In a further embodiment, the present invention provides a method for the prediction of a treatment response in a patient suffering from bladder carcinoma comprising treating the patient with *bacillus* Calmette-Guerin (BCG) intravesical immunotherapy, taking a sample from the patient after the treatment, and testing the sample with a nomogram of cytokines to predict the recurrence of bladder carcinoma.

In further aspects, a method for predicting a quantitative probability of recurrence of bladder cancer in a patient following BCG therapy is provided comprising the steps of: (a) correlating a selected set of factors determined for each of a plurality of persons previously diagnosed with bladder cancer and having been treated by said identified therapy with the incidence of recurrence of bladder cancer for each person of said plurality of persons to generate a functional representation of the correlation, wherein said selected set of factors comprises at least three factors selected from the group consisting of the level (or change in level) of IL-2, IL-6, IL-8, IL-18, IL-1ra, IL-1B, TRAIL, IL-10, IFN-γ, IL-12(p70), IL-12(p40) and TNF-α in a sample from the person, wherein said functional representation of the correlation comprises a different factor evaluation system for each of said factors, and wherein each of said factor evaluation systems provides a value corresponding with a status of said corresponding factor, which value may be summed with values corresponding to the status of the other factors in the selected set to derive a quantitative probability of recurrence of bladder cancer following said identified therapy; (b) determining (e.g., measuring) the status of an identical set of factors for the patient; (c) applying the status of each of the patient's set of factors to said corresponding factor evaluation system to determine the patient's value for each of said factors; and (d) summing the patient's values to derive the quantitative probability of recurrence of bladder cancer in the patient following said BCG therapy.

In still further embodiments, a nomogram useful to predict the likelihood of developing bladder carcinoma in a patient (or of recurrence of a bladder carcinoma in a patient) is provided. For example the nomogram can be constructed using a panel of cytokines, such as urinary cytokines. In certain aspects, the nomogram is predictive of the patient's response to intravesical immunotherapy with BCG. For instance, the nomogram can be the nomogram provided as FIG. 3.

Thus, in certain aspects, there is provided a nomogram for the graphic or virtual representation of a quantitative probability that a patient with bladder cancer will remain free of disease following a BCG treatment. For instance, the nomogram can comprise a plurality of scales corresponding to IL-2, IL-6, IL-8, IL-18, IL-1ra, IL-1B, TRAIL, IL-10, IFN-γ, IL-12(p70), IL-12(p40) and/or TNF-α cytokine level scales (or change is cytokine level scales), a points scale, a total points scale and a predictor scale. In some aspects, the IL-2, IL-6, IL-8, IL-18, IL-1ra, IL-1B, TRAIL, IL-10, IFN-γ, IL-12(p70), IL-12(p40) and/or TNF-α urine level scales (or change in level scales) each have point values on said scales. In further aspects, a nomogram comprises a total points scale that has values that correspond to a predictor scale so that said values on said total points scale may be correlated with values on the predictor scale. Thus, the total points value can be correlated with the predictor scale to predict the quantitative probability of recurrence. In certain aspects, such a nomogram is a graphical representation, such as a representation comprised on a solid support (e.g., a laminated card). In still further aspects, a nomogram is generated with a logistic regression model. In still further aspects, a nomogram is stored in a memory (e.g., a random access memory, read-only memory, a disk, virtual memory, processor, or a database).

In still a further embodiment there is provided an apparatus for predicting a quantitative probability of disease recurrence or progression in a patient with bladder cancer (e.g., a non-muscle-invasive bladder cancer) following a BCG therapy, wherein the apparatus comprises: (a) a correlation of factors determined for each of a plurality of persons previously diagnosed with bladder cancer and having been treated with a BCG therapy with the incidence of recurrence of bladder cancer for each person of said plurality of persons, wherein said factors comprises three or more factors selected from the group consisting of the level (or change is level) of IL-2, IL-6, IL-8, IL-18, IL-1ra, IL-1B, TRAIL, IL-10, IFN-γ, IL-12(p70), IL-12(p40) and TNF-α in a sample from the person urine; and (b) a processor, wherein said processor compares an identical set of factors determined from the patient diagnosed as having bladder cancer to the correlation to predict the quantitative probability of recurrence or progression of bladder cancer in the patient following said identified therapy.

In some aspects a cancer patient of the embodiments is a patient who has or who has been treated for a bladder cancer, such as a non-muscle-invasive bladder cancer. In still further aspects, a patent of the embodiments is bladder cancer patient who has undergone transurethral resection, followed by intravesical BCG treatment.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Bladder cancer affects about 70,000 people each year and is the most expensive tumor in the United States in terms of health care dollars expended per year. The majority of patients are treated with BCG (a vaccine) placed in the bladder via a catheter. There is currently no way to monitor or evaluate an individual patient's response to this immunotherapy beyond waiting to see if the tumor recurs.

The present invention is based on the study of cytokines released into the urine by patients after exposure to BCG. The assay is performed using urine samples obtained from the patient at the last treatment of an induction course of BCG, which is usually at week six at starting treatment.

The inventors studied urine collected from patients who were receiving BCG therapy and assayed the urine for inducible cytokines at various times. From the analysis of the inducible cytokines after the sixth instillation of BCG, nomograms were constructed using the levels of certain cytokines that were able to predict with 82%-85.5% accuracy the likelihood of a patient developing a recurrence. The cytokines included in the nomograms comprise at least 9 cytokines selected from IL-2, IL-6, IL-8, IL-18, IL-1b, IL-10, IL-1ra, TRAIL, IFN-γ, IL-12 (p40), IL-12 (p70), and TNF-alpha. This provides an assay and a device that serves as a surrogate marker for response to intravesical immunotherapy. Such a device enables clinicians to offer tailored therapy to patients with bladder cancer, thus optimizing the timing of curative treatments for this common malignancy.

Using the combination of cytokines described herein and applying the formula shown in the nomogram calculation, the patients that are responding to therapy can be identified with a high degree of accuracy. The strategy to use a panel of urinary cytokines to predict response to BCG is completely novel. While there have been individual cytokines reported as being potentially relevant markers in the literature, this is the first evidence of a panel of markers being useful. In particular, the AUC for assays using the panels were 0.82-0.855, indicating a highly accurate assay.

Figure 5:
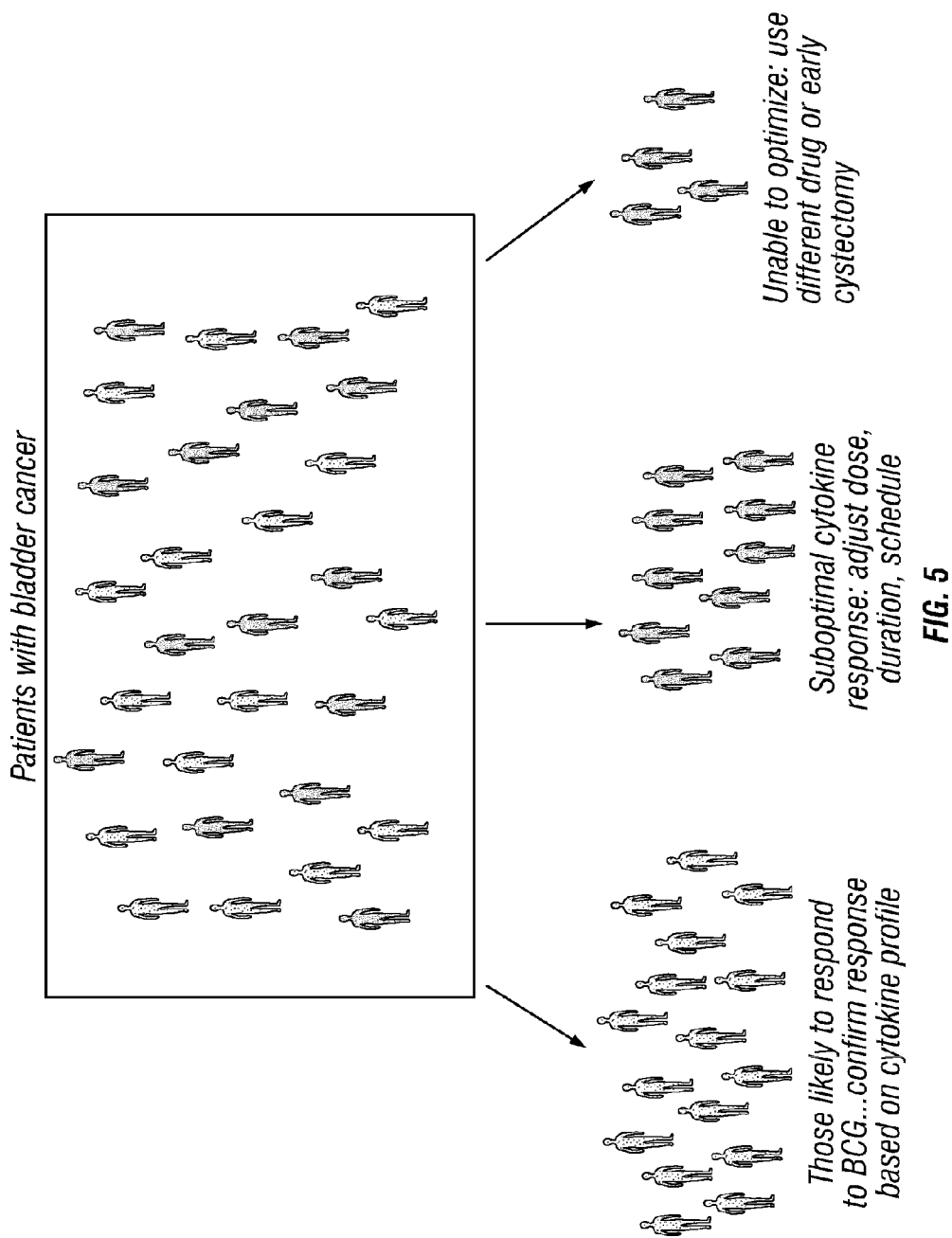
FIG. 5: Potential applications of the present invention. Figure adapted from Johnson (2003).

Embodiments of the present invention provide methods to predict bladder cancer patients who will likely respond to BCG treatment and confirm their response based on the cytokine profile disclosed herein (FIG. 5). The present invention also provides a method to identify subjects with a suboptimal cytokine response, which will allow for adjustments to the dose, duration, and schedule of treatment to optimize the response. In cases where optimization is not achievable, the method will allow for identification of subjects in need of early cystectomy or treatment using a different drug. Furthermore, the test of the present invention is minimally invasive since it is performed on a urine sample produced by the patient.

I. Nomograms

One way in which single, but more often multiple, clinical parameters are utilized by physicians is with the help of nomograms. In the clinical setting, nomograms are representations (often visual) of a correlation between one or more parameters and one or more patient or disease characters. An example of a prevalent clinical nomogram used in determining a prostate cancer patient's likelihood of recurrence is described in Kattan et al., J. CLIN. ONCOL. (1999) 17:1499-1507, and updated in Stephenson et al., J. CLIN. ONCOL. (2005) 23:7005-7012 ("Kattan-Stephenson nomogram"). This nomogram evaluates a patient by assigning a point value to each of several clinical parameters (year of RP, surgical margins, extracapsular extension, seminal vesicle invasion, lymph node involvement, primary Gleason score, secondary Gleason score, and preoperative PSA level), totaling the points for a patient into a nomogram score, and then predicting the patient's likelihood of being recurrence-free at varying time intervals (up to 10 years) based on this nomogram score. An example of a prevalent clinical nomogram used in determining a breast cancer patient's prognosis for survival is the Nottingham Prognostic Index (NPI). See, e.g., Galea et al., BREAST CANCER RES. & TREAT. (1992) 22:207-19.

In this particular case, a nomogram is used for predicting recurrence of bladder carcinoma using changes in cytokines (CC) after treatment with BCG. Thus, embodiments of the invention comprises the specific cytokines and the nomogram used to calculate the values that in turn then predict the risk of recurrence. The model was created using the following steps.

The functional form of CC with regard to risk of recurrence was determined. This was accomplished by dividing CC into quintiles and creating a series of indicator variables corresponding to each quintile, in which the indicator variable was set to 1 if the CC was in that particular quintile and 0 if it was not. The reference group, those in the lowest quintile, was denoted by all indicator variables in the series being set to zero. For example, the minimum, 20th percentile, 40th percentile, 60th percentile, 80th percentile and maximum value for change in IL-2 (ΔIL-2) was −0.2178292, 23.1156, 61.7421, 142.052, 261.463, and 2654.33. Indicator variables were made to represent ΔIL-2 between (a) the 20th and 40th percentiles (23.1156-61.7421), (b) the 40th and 60th percentiles (61.7421-142.052), (c) the 60th and 80th percentiles (142.052-261.463), and (d) the 80th percentile and maximum value (261.463-2654.33). If all four indicator variables were zero, the value of ΔIL-2 was between the minimum value and the 20th percentile. So, if ΔIL-2 was 36.52, the series of indicator variables would have values I20-40=1, I40-60=0, I60-80=0, and I80-max=0. If ΔIL-2 was 150.375, the series of indicator variables would have values I20–40=0, I40-60=0, I60-80=1, and I80-max=0. If ΔIL-2 was 0.0, the series of indicator variables would have values I20-40=0, I40-60=0, I60-80=0, and I80-max=0. The logistic regression was fitted with each cytokine represented in its indicator form and the log odds ratio for these indicator variables were graphed against the midpoint of each quintile interval. If the log-odds ratio graph formed a straight line, this was evidence of a linear risk and therefore CC was kept in the model in its initial continuous form. If the log-odds ratio graph indicated a threshold effect, the CC was dichotomized in such a way as to maximize the −2 log likelihood value of the logistic regression equation.

After a proper functional form was determined, all CCs in their proper functional form were put together in a logistic regression equation. Although backwards selection techniques were initially used to choose a parsimonious model to predict recurrence, other models with different combinations of cytokines were also examined. In addition to measuring the concordance index, the models were examined for sensitivity and specificity. ROC (receiver operating characteristic) curves were graphed to examine the predictive ability of the models. ROC curves are simply a graph of a model's sensitivity vs. the false positive rate. The larger the area under the ROC curve (AUC), the better the model's concordance index and the better the model's ability at predicting recurrence with high sensitivity and specificity. AUC is simply the area that lies under the ROC curve; an AUC of 1 indicates perfect prediction ability—100% sensitivity with 0% false positives. An AUC of 0.5 indicates that random chance is just as accurate at predicting outcome as the model. The closer the AUC is to 1, the better the predictive ability of the model. Concordance index is a measurement of the model's ability to distinguish risk, in other words that that low-risk observations are predicted to be of low probability and that observations at high risk for the event are predicted to occur with high probability. Sensitivity is the proportion of patients that tested positive for recurrence who actually later recurred. Specificity is the proportion of patients who tested negative for recurrence who actually did not recur. The false positive rate is 1 minus the specificity, in other words it is the proportion of patients who tested positive for recurrence but did not actually recur.

A final model was chosen using a subset of cytokines such that the number of cytokines required for the model was minimized while also maximizing the model's predictive ability. So, if three models were candidates for the final predictive model, one that was created with 12 cytokine measurements (IL-2, IL-6, IL-8, IL-18, IL-1ra, IL-1B, TRAIL, IL-10, IFN-γ, IL-12(p70), IL-12(p40) and TNF-α), another than was created with 10 cytokine measurements, and one with only 9, but all three yielded similar sensitivity, the model that used only 9 cytokine measurements was chosen for the final predictive model. In fact, the present model had 9 cytokine measurements—six that contributed change measurements as well as baseline measurements (ΔIL-6, ≤425=0, else=1; ΔIL-18, ≤40=0, else=1; ΔIL-1B, ≤300=0, else=1; ΔIL-12 (p70); IFN-γ, and ΔTRAIL) and three that contributed only change measurements (ΔIL-2, ≤200=0, else=1; ΔIL-8, ≤1,500=0, else=1; and ΔTNF-α).

Figure 3:
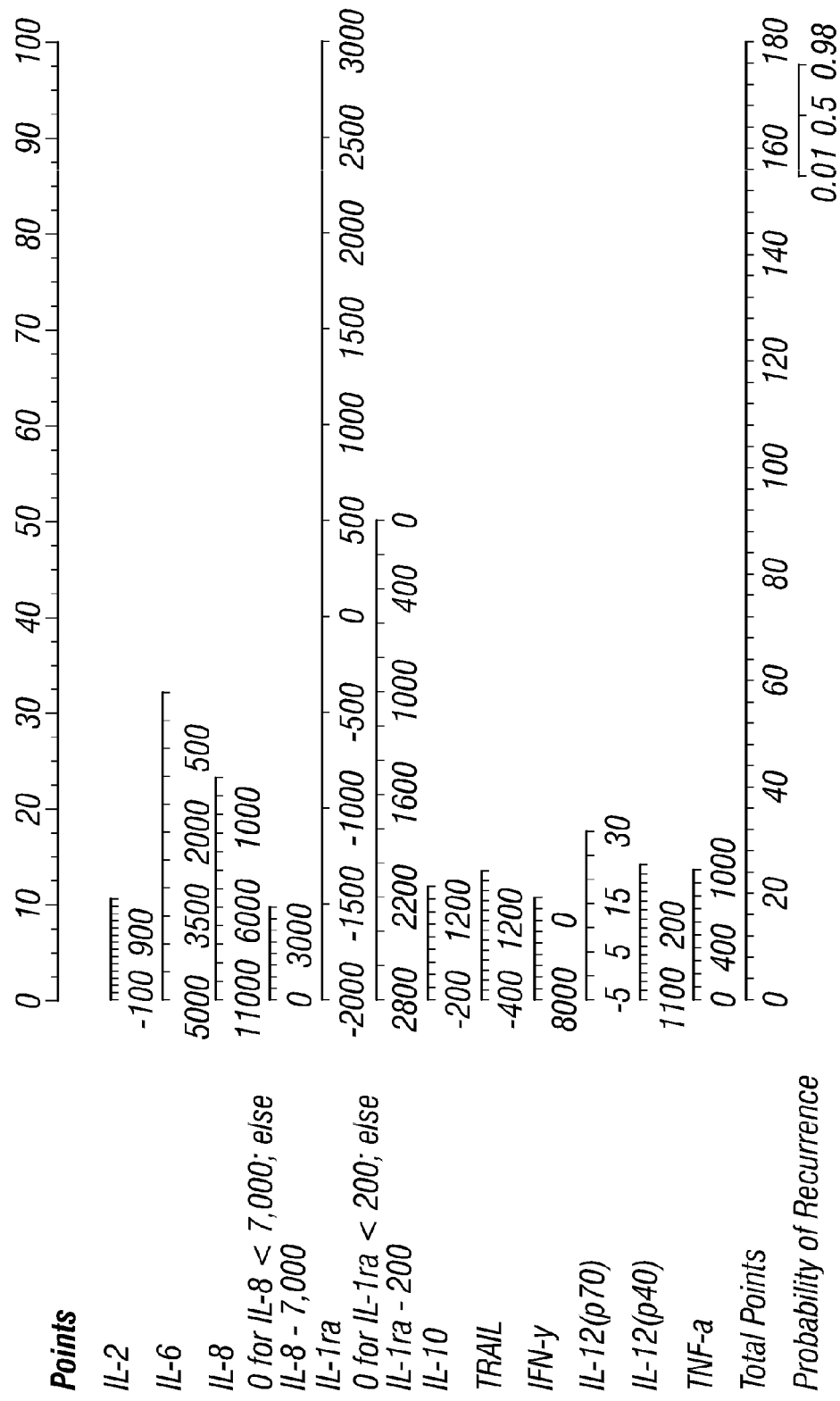
FIG. 3: Example nomogram utilizing cytokines at $6^{th}$ BCG.
Figure 6:
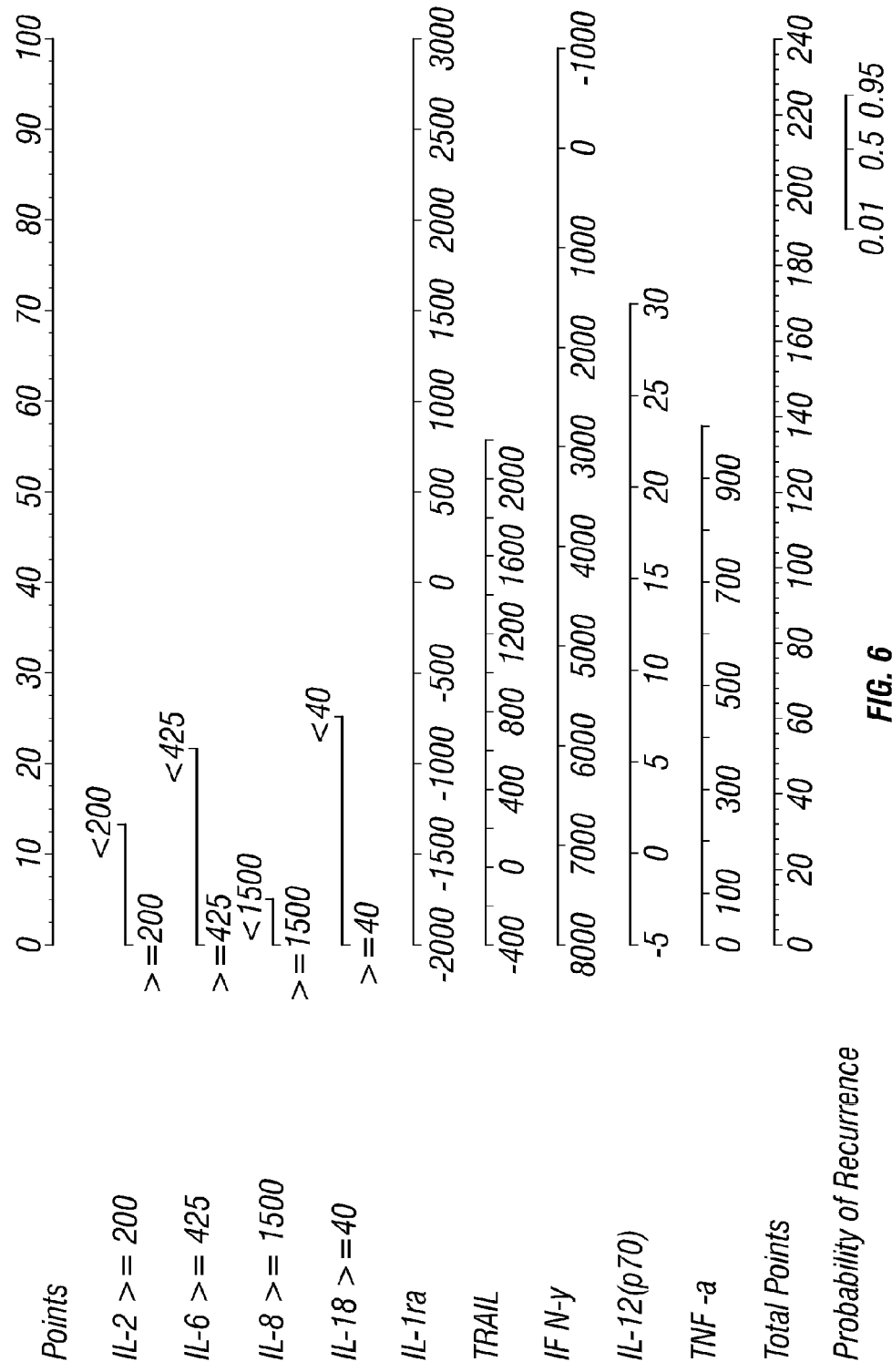
FIG. 6: Example nomogram utilizing cytokines at $6^{th}$ BCG.

The graphical form of the logistic regression equation, i.e., the nomograms shown in FIGS. 3 and 6, was then created to visually display the model. This model was also internally validated using bootstrapping methods. Specifically, a series of 500 simulations were run in which a subset of patients from the original sample were tested using the model and examined for prediction accuracy. This final model that was chosen had high sensitivity (94%) and moderately high specificity (79%). Additionally, it was internally validated and found to have low prediction error as measured by MSE (mean squared error) and size of the absolute error that ranked in the 90th percentile. MSE is the square root of the average of predicted probability of recurrence minus observed probability of recurrence quantity squared, and absolute error is the magnitude of predicted probability of recurrence minus the observed probability of recurrence, with the value at the 90th percentile being larger than the absolute errors associated with 90% of the observations.

II. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Patients. All patients who were scheduled to undergo intravesical BCG immunotherapy at the inventor's center since July 2005 have been offered participation in this prospective, Institutional Review Board-approved clinical trial (National Clinical Trial #01007058). Patients were eligible if they had pathologically confirmed primary or recurrent NMIBC documented within 6 weeks of enrollment and normal upper urinary tract imaging. Pathologic inclusion criteria were similar to the European Organization for Research and Treatment of Cancer intermediate-/high-risk categories (Sylvester et al., 2006). Patients were excluded if they had a history of prior pelvic radiation, had variant histologic subtypes (squamous cell carcinoma, adenocarcinoma, micropapillary, or small cell), or were immunocompromised. All patients with high-grade tumors underwent re-resection between 4 and 6 weeks after the initial diagnosis in order to evaluate for occult muscle invasion. One immediate post-operative intravesical instillation of mitomycin C was administered when appropriate.

Intravesical Immunotherapy. Intravesical BCG was administered according to the protocol used in Southwest Oncology Group trial 8507 (Lamm et al., 2000). All patients received an induction course of BCG consisting of 6 weekly treatments, then maintenance consisting of 3 weekly treatments at 3 and 6 months and then every 6 months for a total of 36 months. Dose reductions were allowed at the discretion of the treating physician. As was reflective of the inventor's practice at the time of study initiation, augmentation of BCG with interferon-α-2b was allowed at the discretion of the treating physician, with the schedule of therapy similar to that outlined above (O'Donnell et al., 2004).

ELISA Assays. Urine samples were collected for cytokine analysis at baseline (after TUR and just prior to initiation of intravesical BCG), at 6 weeks (right before and four hours after the sixth instillation of BCG), and at the third maintenance instillation of BCG (right before and four hours after). Urine was collected at the appropriate time points before and after immunotherapy instillation for later analysis as indicated above. Ten milliliter aliquots were stabilized with a concentrated buffer and a protease inhibitor mixture tablet. The samples were centrifuged at 1,200 rpm for eight minutes, the sediment was discarded and the supernatant stored at −80° C. before analysis. Analysis was performed using a multiplex cytokine assay and inventors were able to identify the panel of urinary cytokines with a complex interaction of change from before to just after the 6th instillation of BCG.

Patient Monitoring. Patients were monitored during BCG treatment according to normal practices at the inventor's institution using cystoscopy and cytology at 3-month intervals for 2 years and 3- to 6-month intervals thereafter. Repeat TUR and other treatments were performed as necessary. Patient management was not mandated based on results of the cytokine assay, but results were provided to the treating physician to be acted upon if so desired.

Statistical Analysis. Patient data were analyzed on an intent-to-treat basis. Descriptive statistics were used to summarize the study population characteristics. Recurrence was defined as any tumor found after the start of intravesical BCG, regardless of grade or stage. Progression was defined as an increase in stage to muscle-invasive disease. Logistic regression was used to assess relationships between patient and tumor characteristics and tumor recurrence or progression. Patient data were censored from time of recurrence, progression, or date of the last documented cystoscopy if recurrence/progression was not observed. Univariate Cox proportional hazards regression was used to model the association between FISH results and risk of recurrence or progression. Multivariate analysis was used to model the association of additional variables with risk of recurrence or progression. The Kaplan-Meier product limit method was used to estimate recurrence-free and progression-free survival. Statistical analyses were performed using STATA/SE version 10.1 statistical software (Stata Corp. LP, College Station, Tex.).

Example 2

Figure 1:
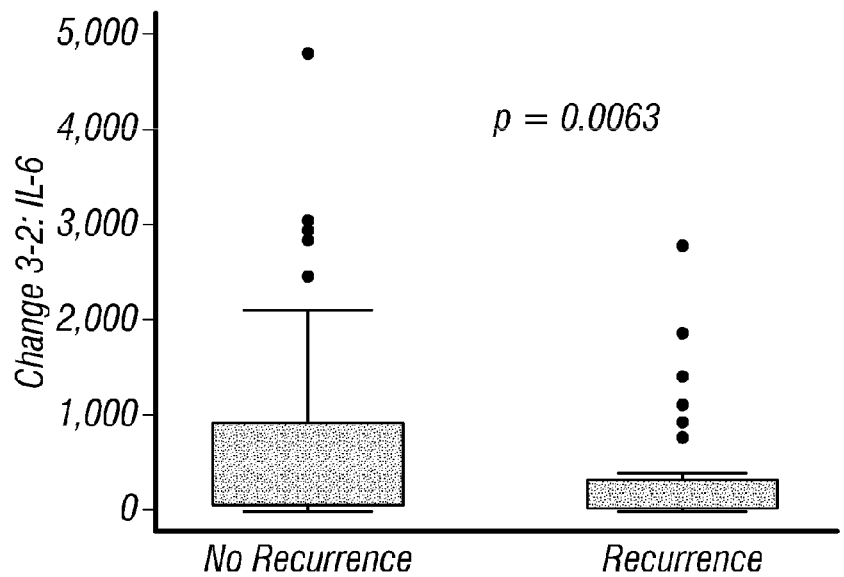
FIG. 1: Increase in uIL-6 with $6^{th}$ BCG. P=0.0063
Figure 2:
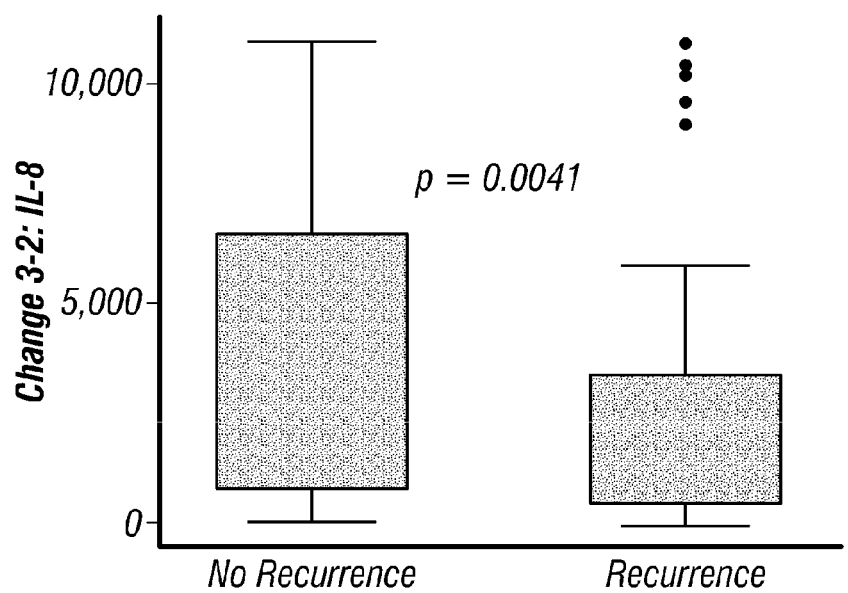
FIG. 2: Increase in uIL-8 with $6^{th}$ BCG. P=0.0041
Figure 4:
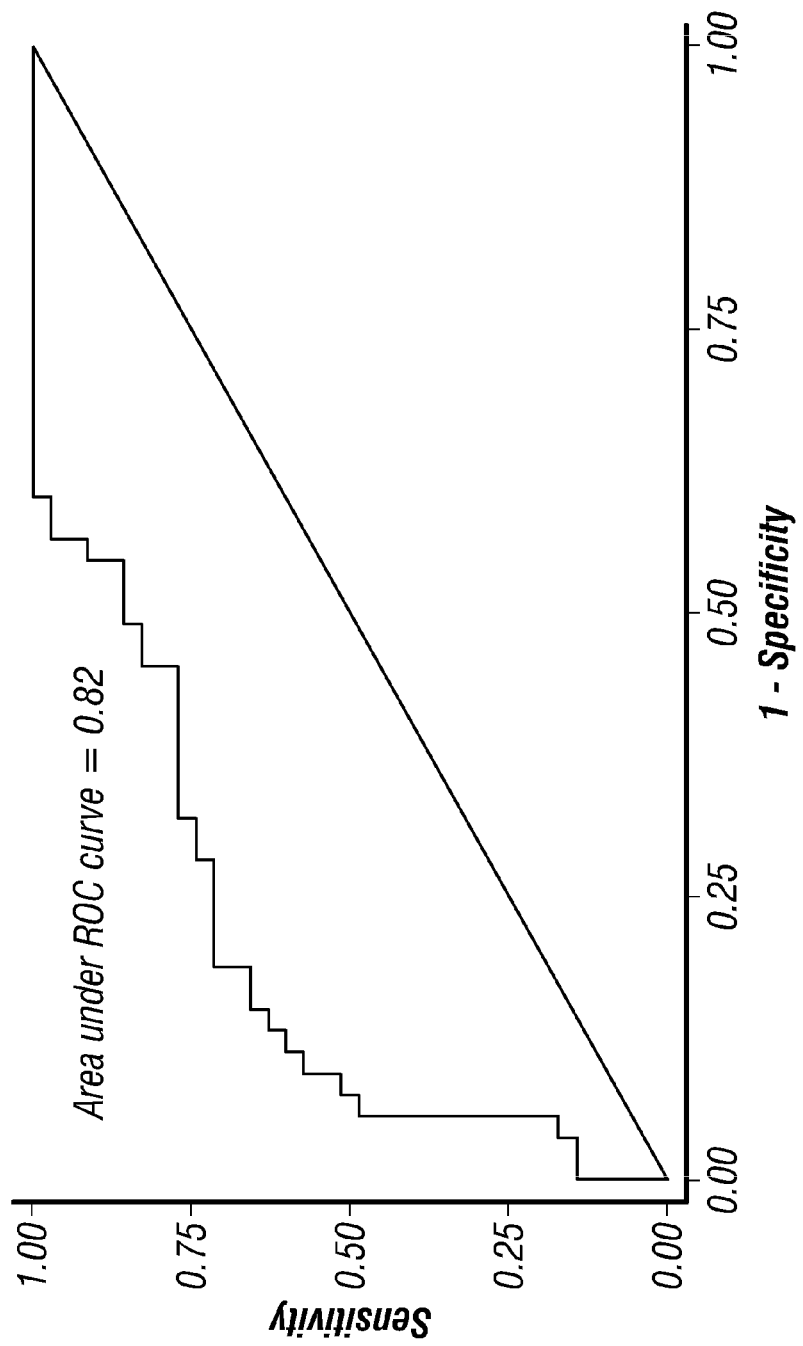
FIG. 4: AUC for cytokine nomogram in FIG. 3. AUC=0.82.
Figure 7:
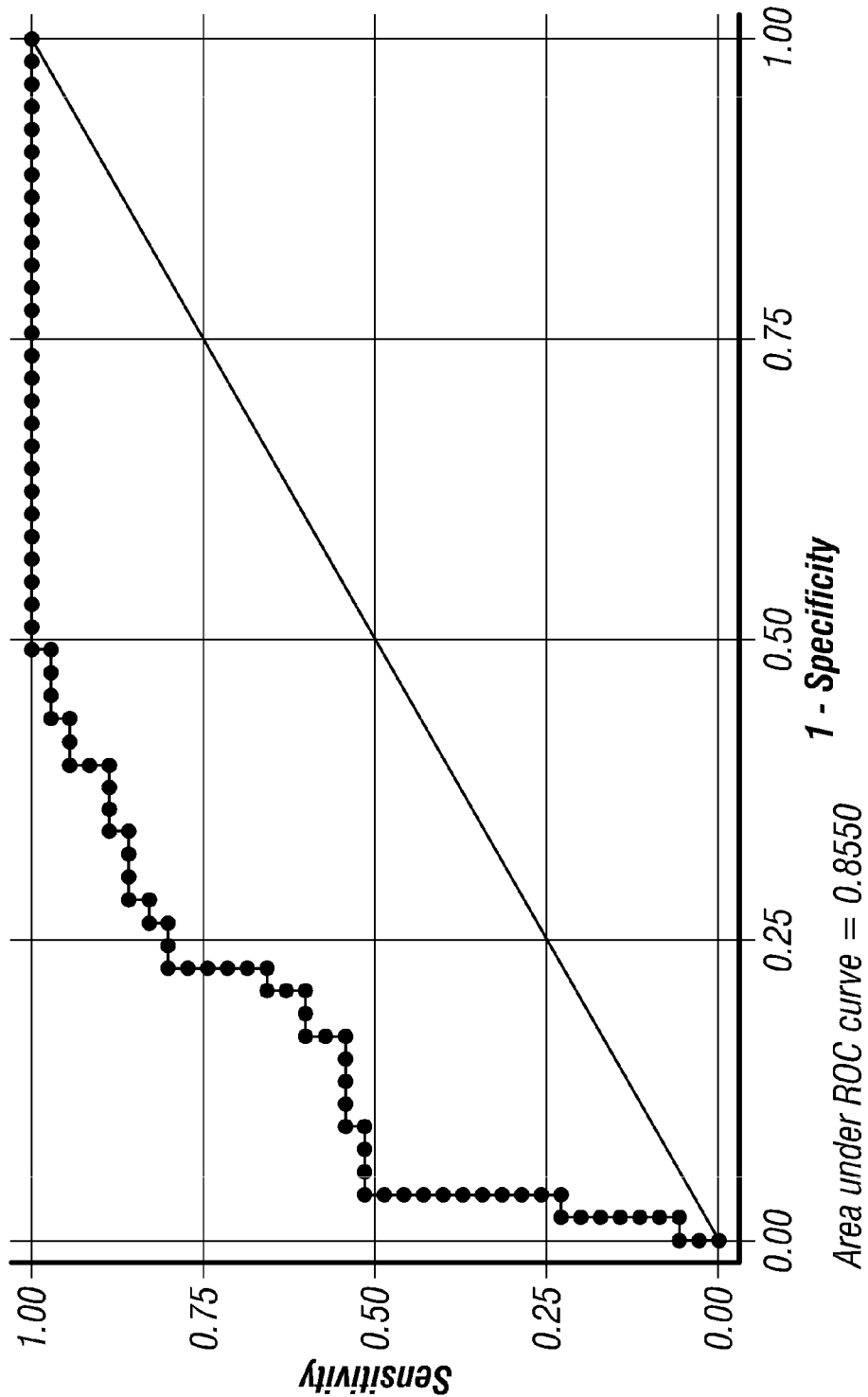
FIG. 7: AUC for cytokine nomogram in FIG. 6. AUC=0.855.

The Identification of a Panel of Urinary Cytokines Useful to Predict Response to BCG Therapy for Bladder Cancer The inventors used the same sampling protocol detailed above in Example 1 and assayed inducible levels of cytokines in response to BCG at weeks. It was found that several cytokines, i.e., IL-6 and IL-8, were individually correlating (FIGS. 1 and 2), which was in agreement with previous work. However, the inventors found that nomograms generated using the change in levels in a panel of cytokines were highly predictive of response to BCG (FIGS. 3 and 6) and were able to predict for recurrence of tumor with AUCs of 82% and 85.5% (95% CI of 77.9%-93.1%), respectively. The nomograms presented in FIGS. 3 and 6 have large AUCs (AUC=0.82 and 0.855, respectively) (FIGS. 4 and 7). No other models using clinical parameters or genes have had such a large AUC.

A nomogram is a model used to predict the probability of an event happening. In this particular case, the inventors are predicting recurrence of bladder carcinoma using changes in cytokines (CC) after treatment with BCG. The invention comprises the specific cytokines and the nomogram used to calculate the values that in turn then predict the risk of recurrence. The model was created using the following steps.

The functional form of CC with regard to risk of recurrence was determined. This was accomplished by dividing CC into quintiles and creating a series of indicator variables corresponding to each quintile, in which the indicator variable was set to 1 if the CC was in that particular quintile and 0 if it was not. The reference group, those in the lowest quintile, was denoted by all indicator variables in the series being set to zero. For example, the minimum, 20th percentile, 40th percentile, 60th percentile, 80th percentile and maximum value for change in IL-2 ($\Delta$IL-2) was −0.2178292, 23.1156, 61.7421, 142.052, 261.463, and 2654.33. Indicator variables were made to represent $\Delta$IL-2 between (a) the 20th and 40th percentiles (23.1156-61.7421), (b) the 40th and 60th percentiles (61.7421-142.052), (c) the 60th and 80th percentiles (142.052-261.463), and (d) the 80th percentile and maximum value (261.463-2654.33). If all four indicator variables were zero, the value of $\Delta$IL-2 was between the minimum value and the 20th percentile. So, if $\Delta$IL-2 was 36.52, the series of indicator variables would have values I20-40=1, I40-60=0, I6080=0, and I80-max=0. If $\Delta$IL-2 was 150.375, the series of indicator variables would have values I20-40=0, I40-60=0, I60-80=1, and I80-max=0. If $\Delta$IL-2 was 0.0, the series of indicator variables would have values I20-40=0, I40-60=0, I60-80=0, and I80-max=0. The logistic regression was fitted with each cytokine represented in its indicator form and the log odds ratio for these indicator variables were graphed against the midpoint of each quintile interval. If the log-odds ratio graph formed a straight line, this was evidence of a linear risk and therefore CC was kept in the model in its initial continuous form. If the log-odds ratio graph indicated a threshold effect, the CC was dichotomized in such a way as to maximize the −2 log likelihood value of the logistic regression equation.

After a proper functional form was determined, all CCs in their proper functional form were put together in a logistic regression equation. Although backwards selection techniques were initially used to choose a parsimonious model to predict recurrence, other models with different combinations of cytokines were also examined. In addition to measuring the concordance index, the models were examined for sensitivity and specificity. ROC (receiver operating characteristic) curves were graphed to examine the predictive ability of the models. ROC curves are simply a graph of a model's sensitivity vs. the false positive rate. The larger the area under the ROC curve (AUC), the better the model's concordance index and the better the model's ability at predicting recurrence with high sensitivity and specificity. AUC is simply the area that lies under the ROC curve; an AUC of 1 indicates perfect prediction ability—100% sensitivity with 0% false positives. An AUC of 0.5 indicates that random chance is just as accurate at predicting outcome as the model. The closer the AUC is to 1, the better the predictive ability of the model. Concordance index is a measurement of the model's ability to distinguish risk, in other words that that low-risk observations are predicted to be of low probability and that observations at high risk for the event are predicted to occur with high probability. Sensitivity is the proportion of patients that tested positive for recurrence who actually later recurred. Specificity is the proportion of patients who tested negative for recurrence who actually did not recur. The false positive rate is 1 minus the specificity, in other words it is the proportion of patients who tested positive for recurrence but did not actually recur.

A final model was chosen using a subset of cytokines such that the number of cytokines required for the model was minimized while also maximizing the model's predictive ability. So, if three models were candidates for the final predictive model, one that was created with 12 cytokine measurements, another than was created with 10 cytokine measurements, and one with only 8, but all three yielded similar sensitivity, the model that used only 9 cytokine measurements was chosen for the final predictive model. In fact, the present model had 9 cytokine measurements—six that contributed change measurements as well as baseline measurements ($\Delta$IL-6, $\leq$425=0, else=1; $\Delta$IL-18, $\leq$40=0, else=1; $\Delta$IL-1ra; $\Delta$IL-12 (p70); IFN-$\gamma$; and $\Delta$TRAIL) and three that contributed only change measurements ($\Delta$IL-2, $\leq$200=0, else=1; $\Delta$IL-8, $\leq$1,500=0, else=1; and ATNF-$\alpha$).

The graphical form of the logistic regression equation [$\eta$=0.2267−2.8594*I($\Delta$IL-2$\geq$200)−4.6366*I($\Delta$IL-6$\geq$425)−1.0933*I($\Delta$IL-8$\geq$1500)−5.4155*I($\Delta$IL-18$\geq$40)+0.00428*$\Delta$IL-1ra+0.00459*$\Delta$TRAIL−0.00235*$\Delta$INF-$\gamma$+0.4328*$\Delta$IL-12(p70)+0.0123*$\Delta$TNF-$\alpha$], i.e., the nomogram shown in FIG. 6, was then created to visually display the model. This model was also internally validated using bootstrapping methods. Specifically, a series of 500 simulations were run in which a subset of patients from the original sample were tested using the model and examined for prediction accuracy. This final model that was chosen had high sensitivity (94%) and moderately high specificity (79%). Additionally, it was internally validated and found to have low prediction error as measured by MSE (mean squared error) and size of the absolute error that ranked in the 90th percentile. MSE is the square root of the average of predicted probability of recurrence minus observed probability of recurrence quantity squared, and absolute error is the magnitude of predicted probability of recurrence minus the observed probability of recurrence, with the value at the 90th percentile being larger than the absolute errors associated with 90% of the observations.

***

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

De Reijke, 1969
Saint, 2002
Esuvaranathan, 1995
Rabinowitz, 1997
Thalmann, 1997
Thalmann, 2000
Ludwig, 2004
Eur Urol., 43:351-361, 2003.
Johnson, Trends in Genetics, 19:660-666, 2003.
Bubendorf et al., Multiprobe FISH for enhanced detection of bladder cancer in voided urine specimens and bladder washings. *Am. J. Clin. Pathol.*, 116:79-86, 2001.
Bubendorf and Grilli, UroVysion multiprobe FISH in urinary cytology. *Methods Mol. Med.*, 97:117-131, 2004.
Caraway et al., Fluorescence in situ hybridization for detecting urothelial carcinoma: a clinicopathologic study. *Cancer Cytopathol.*, 118:259-268, 2010.
Dalbagni et al., Is transurethral biopsy of the bladder necessary after 3 months to evaluate response to *bacillus* Calmette-Guerin therapy? *J. Urol.*, 162:708-709, 1999.
Halling et al., A comparison of cytology and fluorescence in situ hybridization for the detection of urothelial carcinoma. *J. Urol.*, 164:1768-1775, 2000.
Heney et al., Superficial bladder cancer: progression and recurrence. *The Journal of Urology*, 130:1083-1086, 1983.
Herr and Sogani, Does early cystectomy improve the survival of patients with high risk superficial bladder tumors? *The Journal of Urology*, 166:1296-1299, 2001.
Highshaw et al., Is bladder biopsy necessary at three or six months post BCG therapy? *Urol. Oncol.*, 21:207-209, 2003.
Jemal et al., Cancer statistics, 2010. *CA: a cancer journal for clinicians*, 60:277, 2010.
Kamat and Lamm, Immunotherapy for bladder cancer. *Curr. Urol. Rep.*, 2:62-69, 2001.
Kipp et al., Monitoring intravesical therapy for superficial bladder cancer using fluorescence in situ hybridization. *J. Urol.*, 173:401-404, 2005.
Lamm et al., Maintenance *bacillus* Calmette-Guerin immunotherapy for recurrent TA, T1 and carcinoma in situ transitional cell carcinoma of the bladder: a randomized Southwest Oncology Group Study. *J. Urol.*, 163:1124-1129, 2000.
Mengual et al., Clinical utility of fluorescent in situ hybridization for the surveillance of bladder cancer patients treated with *bacillus* Calmette-Guérin therapy. *Eur. Urol.*, 52:752-759, 2007.
O'Donnell et al., Interim results from a national multicenter phase II trial of combination *bacillus* Calmette-Guerin plus interferon alfa-2b for superficial bladder cancer. *J. Urol.*, 172:888-893, 2004.
Sarosdy et al., Clinical evaluation of a multi-target fluorescent in situ hybridization assay for detection of bladder cancer. *The Journal of Urology*, 168:1950-1954, 2002.
Savic et al., The prognostic value of cytology and fluorescence in situ hybridization in the follow-up of nonmuscle-invasive bladder cancer after intravesical *Bacillus* Calmette-Guérin therapy. *Int. J. Cancer*, 124:2899-2904, 2009.

Stein et al., Radical cystectomy in the treatment of invasive bladder cancer: long-term results in 1,054 patients. *J. Clin. Oncol.*, 19:666-675, 2001.

Sylvester et al., Predicting recurrence and progression in individual patients with stage Ta T1 bladder cancer using EORTC risk tables: a combined analysis of 2596 patients from seven EORTC trials. *European Urology*, 49:466-465; discussion 75-77, 2006.

Whitson et al., A multicolour fluorescence in situ hybridization test predicts recurrence in patients with high-risk superficial bladder tumours undergoing intravesical therapy. *BJU International*, 104:336-339, 2009.

Zellweger et al., Multi-target fluorescence in situ hybridization in bladder washings for prediction of recurrent bladder cancer. *Int. J. Cancer*, 119:1660-1665, 2006.

The invention claimed is:

1. A method of treating a patient comprising:
    selecting a patient at risk for cancer relapse following a Bacille Calmette-Guerin (BCG) therapy said patient having been determined to have changes in the levels of IL-2, IL-6, IL-8, IL-18, IL-1ra, IL-1B, TRAIL, IL-10, IFN-γ, IL-12 (p70), IL-12 (p40), and TNF-α following administration of the BCG therapy; and
    administering an anti-cancer therapy to the patient.

2. The method of claim 1, further comprising:
    measuring changes in the levels of IL-2, IL-6, IL-8, IL-18, IL-1ra, TRAIL, INF-γ, IL-12 (p70), and TNF-α in a sample from the patient.

3. The method of claim 2, wherein the sample is a urine sample.

4. The method of claim 2, wherein measuring changes in the levels of the cytokines comprises performing an ELISA.

5. The method of claim 1, wherein the cancer patient is a bladder cancer patient.

6. The method of claim 5, wherein the bladder cancer is a non-muscle-invasive bladder cancer.

7. The method of claim 1, wherein the BCG therapy is an intravesical BCG therapy.

8. The method of claim 1, wherein the anti-cancer therapy is a further BCG therapy.

9. The method of claim 1, wherein the anti-cancer therapy is a chemotherapy, a radiation therapy or a surgical therapy.

10. The method of claim 1, comprising administering an anti-cancer therapy to the patient, if the sample obtained from the patient after BCG therapy comprises an increase in the levels of IL-1ra, TRAIL, IL-12, and TNF-α, and a decrease in the levels of IL-2, IL-6, IL-18, and IFN-γ.

11. The method of claim 10, comprising administering an anti-cancer therapy to the patient, if the sample obtained from the patient after BCG therapy comprises an increase in the levels of IL-1ra, TRAIL, IL-12, and TNF-α, and a decrease in the levels of IL-2, IL-6, IL-8, IL-18, and IFN-γ.

* * * * *